United States Patent [19]

Kurihara et al.

[11] Patent Number: 4,661,162

[45] Date of Patent: Apr. 28, 1987

[54] ENTERIC-SOLUBLE PREPARATIONS

[75] Inventors: Kozo Kurihara; Yuji Otsuka; Toshio Fukazawa, all of Hiromachi, Japan

[73] Assignee: Sankyo Company, Limited, Tokyo, Japan

[21] Appl. No.: 600,308

[22] Filed: Apr. 13, 1984

[30] Foreign Application Priority Data

Apr. 18, 1983 [JP] Japan ................... 58-68037

[51] Int. Cl.$^4$ ........................ A61K 9/32; C08L 1/28
[52] U.S. Cl. ........................... 106/169; 106/162; 106/197.2; 427/3; 424/497
[58] Field of Search ............... 427/3; 514/779, 781; 424/16, 33, 35; 106/169, 197.2, 162

[56] References Cited

U.S. PATENT DOCUMENTS

| | | | |
|---|---|---|---|
| 3,640,741 | 2/1972 | Etes | 514/779 |
| 3,909,444 | 9/1975 | Anderson et al. | 427/3 |
| 4,138,013 | 2/1979 | Okajima | 427/3 |
| 4,287,221 | 9/1981 | Tonedachi et al. | 427/3 |
| 4,341,563 | 7/1982 | Kurihara et al. | 106/191 |
| 4,497,847 | 2/1985 | Kurihara et al. | 427/3 |
| 4,533,562 | 8/1985 | Ikegami et al. | 427/3 |

FOREIGN PATENT DOCUMENTS

EP63014 10/1982 European Pat. Off. ............... 427/3

Primary Examiner—Ronald W. Griffin
Attorney, Agent, or Firm—Frishauf, Holtz, Goodman & Woodward

[57] ABSTRACT

An enteric-soluble composition for coating drugs and the like comprises a conventional enteric-soluble polymer in admixture with a polyanionic polymer which is soluble at low pH values. By altering proportions and types of both polymer, it is possible to alter the pH value at which the composition will disintegrate to release the drug or the like.

40 Claims, No Drawings

ENTERIC-SOLUBLE PREPARATIONS

BACKGROUND OF THE INVENTION

The present invention relates to enteric-soluble preparations.

Enteric-soluble preparations are normally prepared using a film-forming substance which is soluble in the intestinal juices. The pH value at which commercially available film-forming substances dissolve is about 6.8, which means that enteric-soluble preparations made of such a film-forming substance should also disintegrate at about pH 6.8. However, there is a need for enteric-soluble preparations that will disintegrate at pH values below 6.8, and particularly values in the range from 3 to 6, since the pH value in the duodenum after a meal is normally about 3.5 and because the pH values in the stomach and intestines vary from time to time in each individual and also vary between individuals.

No available film-forming substance appears to meet this requirement.

The bioavailability of known enteric-coated preparations varies significantly at each administration between individuals or even in the same individual, both in terms of the quantity released and the rate of release of the active component; this contrasts with conventional preparations administered orally, where amounts and rate of release are reasonably predictable. This inevitably gives rise to uncertainties as to the effectiveness of enteric-coated preparations. Moreover, it is a common observation that the average bioavailability of enteric-coated preparations is lower than that of other preparations. This is partly because of variations in the pH in the digestive organs between individuals or in the same individual but at different times and partly because it is difficult to be certain that the enteric-soluble membrane surrounding the preparation will dissolve, disperse or disintegrate sufficiently rapidly and certainly in the digestive organs, particularly in the small intestines.

For example, if a drug is administered in a single enteric-soluble unit dose (e.g. a tablet), which can be absorbed only in the upper small intestine, bioavailability will be 0% if, for any one of many reasons, the dose does not happen to disintegrate in the upper small intestine and, as a result, the drug may not be utilised at all. In order to avoid this risk, administration is sometimes effected by means of a large number of small unit doses (for example a number of enteric-soluble granules contained together in a conventional capsule). Administration in this way, however, means that at each administration the bioavailability is the average of the actual bioavailabilities of the individual granules, which is therefore less than the theoretical maximum of 100%. Accordingly, although this expedient has the effect of ensuring the there is a reasonable likelihood that at least some of the active ingredient given with each administration is utilised, it does not improve the overall average bioavailability.

The reasons for administering drugs orally in the form of enteric-soluble preparations can be summarised as follows:

(1) prevention of decomposition of drugs that are unstable at pH values lower than a certain level;

(2) prevention of side effects brought about by the release of drugs in the stomach;

(3) prevention of dilution of drug concentration in the intestines, attributable to disintegration of drugs in the stomach and their subsequent movement to the intestines; and (4) prolonged effect.

Although such preparations are referred to generally as "enteric-soluble preparations", there are, in fact, various types depending upon their functional requirements, as the object of using them can be different, as described above. Thus, they can be divided into the following types:

A. Those that do not release drugs in the stomach, that is to say, the enteric-soluble preparations which do not undergo dissolution, dispersion or disintegration at the pH value in the stomach of an ordinary person, and the drug is not released in the stomach through the membrane of the preparation.

B. Those that do not need to specify the site at which disintegration takes place; these preparations will not undergo dissolution, dispersion or disintegration at pH values below a specified value, and outside liquids will not permeate into such preparations through the membrane, but they do undergo dissolution, dispersion or disintegration of pH values higher than this specified value.

C. Those that undergo dissolution, dispersion or disintegration at a specified site, particularly at a specified site in the intestines, regardless of the pH value.

Of these three types of preparations, quite special ones are known for type C; these special preparations are monitored from outside the body after administration (e.g. by X-ray projection) to determine their position in the digestive organs and, when they reach the desired site, the drugs contained therein are released by the joint action of an electro-magnetic pulse emitted from outside the body and of the counterpart receiver contained in the preparation. The present invention is not aimed at such special types of preparations but at enteric-soluble preparations of types A and B.

As regards the pH value in the digestive organs, the following is known from the literature:

1. pH in the stomach

The pH value in the stomach of an ordinary person after a meal is 1.67. It reaches 3.0 at the highest, even when all the acid is combined with protein. (Howell, W. H., "A Textbook of Physiology", 13th ed., Saunders, Philadelphia, 1938, page 82, 858).

The pH value in the stomach of 137 persons who had no history of stomach disease or anaemia was determined. 65% were in the range pH 1.5–2.5 and 86% were in the range pH 1.5–3.5 after having a proteinaceous meal. [Levin, E., et al., J. Lab. Clin. Med., 38, 828 (1951); Bernstein, R. E., ibid., 40, 707 (1952)].

The pH value in the stomach of a human is normally between 1 and 3.5, mostly between 1 and 2.5. (Wagner, J. G., "Biopharmaceutics and Relevant Pharmacokinetics", 1st Ed., Hamilton Press, Illinois, 1971, page 3).

The pH value in the stomach after a meal is controlled by itself by virtue of a feed-back mechanism. Namely, the release of gastrin to the blood stops at a pH value below 1.8–2.0 and reaches the maximum at a pH value above 3.0. (Yoshitoshi, Y., et al, "Biochemistry of Diseases, Vol. 13B, Digestive Organs", Nakayama Shoten, Tokyo, 1976, page 3).

The pH value in the empty stomach of 83 patients (64 males and 19 females, of whom 17 were healthy; of the remainder, there were 43 cases of chronic gastritis, 39 cases of gastric ulcers, 10 cases of duodenal ulcers, and 5 cases of gastric tumours) was determined with an antimony electrode capsule for the pH measurement.

All values fell within the range of 0.2–2.5. (Kawai, K., "Stomach, Its Shape and Function", Igaku Shoin, Tokyo, 1975, page 83).

2. pH in the small intestine

The pH value in the small intestine is normally from 5 to 7. It goes up along the intestine and may reach 7–8 in the lower small intestine. (Wagner, J. G., op. cit. page 3).

The pH value in the empty duodenum is about 6.5, whereas it is about 3.5 after a meal. (Yoshitoshi. Y, et al., op. cit. page 8).

In view of the above-mentioned literature, it would appear that the properties required for type A enteric-soluble preparations are such that they are resistant to dissolution, dispersion or disintegration at pH values below 3.0 or perhaps 4.0 but are susceptible at a pH value slightly higher than 4.0. Further consideration should be given, however, to cases in which release of drugs in the stomach should be avoided as much as possible, or to those individuals having less acid in their stomachs, where the pH value may be about 5. In these cases, the pH value at which rapid dissolution, dispersion and disintegration take place should be designed to be much higher.

The pH value of artificial enteric juice, as prescribed in the Pharmacopoeias of many countries is about 7.0. However, for the reasons mentioned above, this does not fully comply with practical requirements. Rather, it is considered preferable to design for enteric-soluble preparations to disintegrate at a pH value as low as 6.0 in view of the information noted above.

Further, in order to ensure the bioavailability of drugs whose absorption site is limited, for instance, to the upper intestine, it is quite insufficient only to ensure that they dissolve, disperse or disintegrate at pH 6, in view of the pH values in the duodenum, namely about 3.5 after a meal, as described above. Therefore, it is considered desirable for type B preparations to dissolve, disperse or disintegrate rapidly at the lowest possible pH value within the permissible range.

For these reasons, enteric-soluble preparations should be designed to disintegrate as quickly as possible at any pH value between 3 and 6, and it is an object of this invention to provide such enteric-soluble preparations. In other words, it is to provide preparations (and specifically the membrane thereof) that would not allow outer liquid to permeate into the preparations or allow the drugs to release themselves through the membrane at a pH value lower than 1–2, but which dissolve, disperse or disintegrate at any pH value higher than this.

Disintegration of enteric-soluble base polymers so far known was examined and, as a result, it was found to be insufficient at pH values lower than 6.0 with almost all polymers.

BRIEF SUMMARY OF THE INVENTION

It is an object of the present invention to provide a composition which can be used as the enteric-soluble membrane on an enteric-soluble preparation and which is capable of being targeted at a chosen pH within the range from 3 to 6.

Accordingly, the present invention provides an enteric-soluble composition comprising a mixture of an enteric-soluble polymer with a polyanionic polymer which is soluble in or permeable to a liquid having a pH value less than or equal to 2. Preferably said mixture is soluble in a liquid having a pH value which is above a chosen pH value within the range from 3 to 6 and is insoluble in a liquid having a pH value below said chosen pH value.

The invention also provides an enteric-soluble preparation in unit dosage form comprising an active ingredient surrounded by a membrane formed from said enteric-soluble composition.

DETAILED DESCRIPTION OF INVENTION

The polyanionic polymer which is one of the components of the composition of the invention is a film-forming polymer which is soluble in or permeable to liquids having a relatively low pH, specifically, at pH values equal to or less than 2, and generally at pH values from 1 to 2. At such pH levels, the polymer will dissolve, disperse or disintegrate or, at the least, become permeable to the liquid, thus allowing liquid to permeate into the interior of the polymer-coated preparation. In practice, this would mean that it would allow the release of drugs from inside the preparation to the outside at pH values much lower than desired. Examples of polyanionic polymers include alginic acid, polypectinic acid and carboxymethylcellulose, as well as salts thereof. Certain of these polymers have been suggested for use as enteric-soluble base polymers in Japanese Patent Specifications Kokai No. 76415/76 and 76413/76. However, although a membrane consisting only of such a polymer may still maintain its form at pH values within the range from 1 to 2, such polymers may not be used in practice by themselves as the enteric-soluble membrane, as they nonetheless allow significant permeation of liquid into and diffusion and release of drugs through the preparation, due to the strong semi-permeability of such a membrane at these pH levels.

The polyanionic polymer may be used in the form of the free acid or in the form of a salt. Suitable salts include salts with: alkali metals, such as sodium or potassium; alkaline earth metals, such as calcium or magnesium; or organic amines, such as stearylamine, triethanolamine or basic amino acids. Alternatively, it can be used in the form of a salt-like complex with a polycationic polymer, such as polyvinylacetal diethylaminoacetate. Of course, mixtures of such salts and/or such complexes may also be used.

Examples of suitable enteric-soluble polymers include ethyl acrylate/methacrylic acid copolymers, methyl acrylate/methacrylic acid copolymers, methyl methacrylate/methacrylic acid copolymers, carboxymethylethylcellulose, cellulose acetate phthalate, starch acetate phthalate, cellulose acetate succinate, styrene/maleic acid copolymers, cellulose benzoate phthalate, methylcellulose phthalate, ethylhydroxyethylcellulose phthalate, cellulose acetate maleate, hydroxypropylmethylcellulose phthalate, amylose acetate phthalate, polyvinyl alcohol phthalate, polyvinyl acetate phthalate, polyvinyl propionate phthalate, polyvinyl butyrate phthalate, polyvinylacetoacetal phthalate, polyvinylacetoacetal succinate, vinyl acetate/maleic anhydride copolymers, styrene/maleic anhydride copolymers, methyl vinyl ether/maleic anhydride copolymers, ethylene/maleic anhydride copolymers, acrylonitrile/methyl acrylate/maleic anhydride copolymers, butyl acrylate/styrene/maleic anhydride copolymers, styrene/acrylic acid copolymers, butyl acrylate/styrene/acrylic acid copolymers, cellulose propionate phthalate and vinyl acetate/crotonic acid copolymers.

Where the enteric-soluble polymer is acidic in character, it may, like the polyanionic polymer, be used as such or in the form of a salt or salt-like complex, examples of which are given in relation to the polyanionic polymer.

Of the polyanionic polymers listed above, alginic acid is particularly preferred. This is because alginic acid is a copolymer of D-mannuronic acid and L-guluronic acid and different varieties of alginic acid in which the ratio of mannuronic and guluronic acids varies are available; moreover, the molecular weight of the polymer can be altered by various well known techniques, such as heating. Accordingly, by using different types and/or molecular weights of alginic acid, it is possible to control the pH profile at which dissolution, dispersion or disintegration of the composition of the invention will occur.

Of the enteric-soluble polymers listed above, carboxymethylethylcellulose (CMEC) is most preferred, since it is highly stable to hydrolysis and coagulation in water-based coating compositions, for which commercial demand is at present highest.

The molecular weight of the enteric-soluble polymer and of the polyanionic polymer are each preferably such that the viscosity of a 1% by weight aqueous solution thereof at 25° C. and at pH 7.0 is not greater than 500 cps, when measured with a Brookfield viscometer, except where some special delay in the release of the drugs is desired.

Accordingly, by means of the present invention, it is possible to obtain preparations which do not undergo dissolution, dispersion or disintegration, permeation of liquid thereinto or release of drugs therefrom at pH values in the range of from 1 to 2, but do undergo this at pH values greater than 2. Control of the pH and the time at which the enteric-soluble membrane allows release of drugs contained therein to take place can be achieved, as discussed above, by appropriate choice of the enteric-soluble polymer and of the variety, molecular weight and amount of polyanionic polymer.

Solubility of said polyanionic polymer and of said mixture is determined by immersing a tablet coated with said polymer or said mixture in a liquid selected from the group consisting of the first liquid of the Japanese Pharmacopoeia 10th edition, the second liquid of said Pharmacopoeia and mixtures of said first and second liquids at a temperature of 37° C., said polymer or said mixture of polymers being soluble if the average time of six such coated tablets to dissolve, disperse or disintegrate in said liquid does not exceed 60 minutes and being insoluble if said time exceeds 120 minutes and if said polymer or said mixture of polymers does not become permeable within 120 minutes.

It is difficult to define generally the ratio of enteric-soluble polymer to polyanionic polymer as the various different enteric-soluble and polyanionic polymers which can be used behave in different ways and hence different polymers could be expected to be present in the composition to different proportions in order to achieve dissolution etc at the chosen pH value; moreover, of course, the ratio of the two types of polymer will vary depending upon the particular pH chosen. Speaking generally, the weight ratio of enteric-soluble polymer to polyanionic polymer is preferably from 20:1 to 0.5:1 and, since it is normally preferred that the enteric-soluble polymer should be the major constituent, whilst the polyanionic polymer is the minor constituent, a more preferred ratio is from 10:1 to 1:1. The most preferred ratio is about 9:1. However, it should be appreciated that these ratios are given only for the purposes of general guidance and the precise ratio chosen will depend upon many factors in each individual case, which can easily be determined by simple experiment.

The main effect of varying the molecular weight of a polyanionic polymer to be added to an enteric-soluble polymer in accordance with the present invention is on the time required for the mixture to dissolve, disperse or disintegrate, rather than on the pH at which such dissolution, dispersion or disintegration takes place.

The enteric-soluble composition of the present invention may be coated onto a drug in any conventional form, such as a tablet, capsule, pill, granule or powder, to form the desired preparation. Preferably, the composition is employed for coating in the form of an aqueous solution or suspension and, since aqueous systems are preferred in current commercial usage, the invention will hereafter be described primarily with reference to such system. However, it will be appreciated that non-aqueous media may be employed, as is well known in the art. The solid drug formulations may be coated with the composition of the invention by various conventional means, for example by spraying or painting a solution or suspension of the composition onto the formulation or by immersing the formulation in a solution or suspension of the composition. Various conventional coating apparatus may be employed to facilitate this, including, for example, a centrifugal fluidised bed coating apparatus, a pan coating apparatus or a fluidised bed granulating coating apparatus.

After the solid formulation has been coated with the composition of the invention, other conventional procedures may be followed, including polishing, sugar coating or additional coating using another coating agent. Also, of course, the solid formulation may be coated with another coating agent prior to application of the enteric-soluble composition of the invention.

The enteric-soluble composition of the invention may, if desired, contain such conventional additives as plasticisers, film-forming materials, film-forming aids, polymer particles and/or surfactants as dispersing agents for the polymers or plasticisers, colouring agents, fillers (such as titanium dioxide, talc or barium sulphate) or antioxidants, in order to improve the properties of the preparations, as is well known to those skilled in the art.

The invention is further illustrated by the following Examples, in which all parts are by weight.

EXAMPLE 1 AND COMPARATIVE EXAMPLE 1

(a)

Preparation of Uncoated Tablets 10 parts of the sodium salt of M-4 carboxylic acid (an anti-hyperlipaemic agent, as described in U.S. patent application Ser. No. 270,846 filed June 5, 1981, now U.S. Pat. No. 4,346,227), 107.75 parts of lactose and 30 parts of a partially substituted hydoxypropylcellulose (manufactured by Shin-Etsu Chemical Co. Ltd., in which from 7 to 16% of the original hydroxy groups had been replaced by hydroxypropyl groups; this is insoluble in water) were mixed in a mortar. To the mixture were added 30 parts of a 5% w/v aqueous solution of a low viscosity hydroxypropylcellulose (manufactured by Nippon Soda Co. Ltd.; in which less than 60% of the original hydroxy groups had been replaced by hydroxypropyl groups; the viscosity of a 2% w/v aqueous solution at 20° C. being 6.0-10.0 cps; soluble in water) and a suitable amount of water, and the resulting mixture was mixed in a kneader. The mixture was then granulated with a Tornado Mill (manufactured by Stokes Company, USA) with a screen having square apertures 10×10 mm. The granules were dried in a draught drier for 1 hour at 60° C. and then passed through a Tornado Mill provided with a screen having circular apertures of 1 mm diameter.

149.25 parts of the resulting granules and 0.75 part of magnesium stearate were mixed in a V-shaped mixer, and the mixture was then tableted into biconvex tablets of diameter 7 mm and weight 150 mg.

The tablets were tested using the disintegration tester prescribed by the Japanese Pharmacopoeia, 10th edition, without a disc. The disintegration time was about 5 minutes, whether the liquid used was water or the first or the second liquids prescribed by said Japanese Pharmacopoeia.

(b)

Preparation of Fine Carboxymethylethylcellulose 1500 g of a 0.5N aqueous solution of sodium hydroxide were added to a suspension of 450 g of CMEC in 11550 g of water, to dissolve the CMEC. The resulting liquid was passed through a 150 Tyler mesh sifter to remove insolubles and impurities. 1500 g of 0.5N hydrochloric acid were then added to the solution at room temperature whilst mixing under a high rate of shear. The mixture was then heated to 80° C. and stirred at that temperature for 10 minutes, after which it was cooled to about room temperature and the fine CMEC was collected by filtration and washed. The resulting powder was dried in a draught drier at 60° C. for 1 hour.

The fine CMEC thus obtained had a particle diameter of 1-2 micrometers, determined by optical and scanning electron microscopes.

(c)

Preparation of Coating Liquid—Comparative Example 1

10 parts of fine CMEC, 3 parts of a mixture of mono- and di-caprylates of glycerin (manufactured by Nikko Chemical Co. Ltd., grade MGK) and 0.5 part of polysorbate 80 were stirred in 86.5 parts of water to prepare a solution/suspension.

(d)

Preparation of Coating Liquid—Example 1

9 parts of fine CMEC, 3 parts of a mixture of mono- and di-caprylate of glycerin (MGK), 0.5 part of polysorbate 80 and 1 part of sodium alignate (type IL$_2$, manufatured by Kimitsu Chemical Industry Co. Ltd.) were stirred with 86.5 parts of water to give a solution/suspension.

(e)

Coating

The tablets prepared as described in step (a) above were pre-coated with a small amount of a mixture prepared by mixing equal volumes of a 5% w/v solution of hydroxypropylmethylcellulose in ethanol and methylene chloride, since the active principal in the tablets tends to decompose on contact with an acid.

The tablets were then coated with the coating liquid of Comparative Example 1 or of Example 1. Specifically, 300 g of the pre-coated tablets were placed in an octagonal laboratory pan of diameter about 25 cm and then coated using a two-fluid spraying gun under a pressure of 1-2 kg/cm$^2$. The tablets were subjected to repeated spraying and drying cycles (the inlet temperature of the air employed for the drying cycles was about 65° C.) until the weight of each tablet had increased as a result of the coating by about 23 mg.

(f)

Tests and Results

The coated tablets prepared as described above were tested in the disintegration tester prescribed by the Japanese Pharmacopoeia, 10th edition, either with or without a disc. 6 tablets were used for each test.

The liquids tested were either the first liquid of the Japanese Pharmacopoeia (simulated gastric juices) alone, which had a pH of 1.2, or a mixture of the first liquid with the second liquid of the Pharmacopoeia (simulating intestinal juices) in various proportions to achieve the desired pH value. The results obtained, in terms of the disintegration time in minutes, averaged over the six tablets are shown in Table 1; in parentheses are shown the range of disintegration times.

TABLE 1

| Test liquid | Disc | Example 1 | Comp. Ex. 1 |
| --- | --- | --- | --- |
| pH 1.2 | no | >120 | >120 |
|  | yes | >120 | >120 |
| pH 4.0 | no | 36 | 81 |
|  |  | (30–42) | (48–119) |
| pH 5.0 | no | 34 | 68 |
|  |  | (30–40) | (29–99) |
| pH 6.0 | no | 26 | 56 |
|  |  | (23–30) | (43–63) |

(g)

Conclusions

The tablets of Example 1 were shaken in the first liquid (pH 1.2) for 2 hours, after which the tablets still appeared to be intact; the amount of active principal remaining in the tablets after this time, measured by high pressure liquid chromatography, was 99.3% of that originally present. These results indicate that the tablets disintegrate rapidly at pH values as low as 4.0, even though no decomposition or dissipation of the active principal would seem to have taken place at the lower pH value of 1.2. This clearly shows that the coating of Example 1 is suitable for type B enteric-soluble preparations, which are particularly useful for drugs whose site of absorption is limited to the upper small intestine or where rapid absorption is desired.

EXAMPLE 2

(a)

Preparation of Uncoated Tablets 10 parts of the same active principal as was used in Example 1, 48.875 parts of lactose and 15 parts of partially substituted hydroxypropylcellulose (the same as was used in Example 1) were mixed for about 3 minutes in a Henschel mixer (Mitsui Miike Seisakusho, Japan). To the mixture were then added 15 parts of a 5% w/v aqueous solution of low viscosity hydroxypropylcellulose (the same as was used in Example 1) and an appropriate amount of water, and the whole mixture was kneaded. The mixture was granulated in a Tornado Mill with a screen having square apertures of dimensions 10×10 mm and the resulting granules were dried in a draught drier for 1 hour at 60° C., before being passed through a Tornado Mill whose screen had circular apertures of diameter 1 mm.

74.625 parts of the granules thus obtained and 0.375 g of magnesium stearate were mixed in a V-shaped mixer, and then the mixture was tableted into biconvex tablets having a diameter of 6 mm and each weighing 75 mg. The disintegration time of the tablets were tested by the method prescribed in the Japanese Pharmacopoeia, without a disc, and the disintegration time was about 5 minutes in water, as well as in the first and second liquids.

(b)

Preparation of Coating Liquid 9 parts of fine CMEC prepared as described in Example 1, 3 parts of a mixture of mono- and di-caprylates of glycerin (MGK) 0.5 part of polysorbate 80 and 1 part of sodium alginate (type IL$_2$) were stirred in 86.5 parts of water to give a solution/suspension.

(c)

Coating

Coating was effected as described in Example 1(d) save that the actual weight of the solid increase was about 13 mg.

(d)

Results

The disintegration time at various pH values was measured with the distintegration tester prescribed by the Japanese Pharmacopoeia. 6 tablets were used for each test and the results, in minutes, are given in Table 2.

TABLE 2

| Test liquid | Disc | Disintegration time (mins.) |
| --- | --- | --- |
| pH 1.2 | no | >120 |
|  | yes | >120 |
| pH 4.0 | no | 23 |
|  |  | (17–26) |
| pH 5.0 | no | 26 |
|  |  | (22–31) |
| pH 6.0 | no | 20 |
|  |  | (18–23) |

(e)

Conclusions

It is clear from the above results that the coated tablets disintegrate rapidly at pH values within the range from 4.0 to 6.0, but do not disintegrate within 2 hours at low pH values, thus indicating that the composition of the invention may be useful for type B enteric-soluble preparations.

EXAMPLES 3 to 5 and COMPARATIVE EXAMPLE 2

(a)

Preparation of Coating Solution—Comparative Example 2

The coating solution used was the same as that used for Comparative Example 1.

(b)

Preparation of Coating Solution—Example 3

9 parts of fine CMEC, 3 parts of a mixture of mono- and di-caprylates of glycerin (MGK), 0.5 part of polysorbate 80 and 1 part of alginic acid (regular type, manufactured by Kimitsu Chemical Industry Co. Ltd.) were stirred with 86.5 parts of water, to form a solution/suspension.

(c)

Preparation of Coating Solution—Example 4

A coating solution was prepared as for Example 3, except that the alginic acid used was Snow acid algin, manufactured by Fuji Chemical Industry Co. Ltd.

(d)

Preparation of Coating Solution—Example 5

A coating solution was prepared as in Example 3, except that the alginic acid used was Duck acid, manufactured by The Kamogawa Chemical Industry Co. Ltd.

(e)

Preparation of Casting Film

Each coating solution, prepared as described above, was poured onto a petri dish and dried for 24 hours at 40° C. to give a casting film of thickness 100 micrometers.

(f)

Tests 5 glass beads (each weighing about 145 mg) were added to a 10 ml beaker containing 5 ml of one of the test liquids shown in Table 3. A test piece of the casting film (dimensions 1×1 cm, thickness about 100 micrometers) was then added to each beaker and the beaker was shaken at 80 shakes per minute and a temperature of 37° C. The piece was observed to determine whether dissolution, dispersion or disintegration took place. The time required for dissolution, dispersion or disintegration (in minutes) is shown in Table 3.

TABLE 3

| pH of Test liquid | Ex. 3 | Ex. 4 | Ex. 5 | Comp. Ex. 2 |
| --- | --- | --- | --- | --- |
| pH 1.2 | >60 | >60 | >60 | >60 |
| pH 4.0 | >60 | >60 | 15 | >60 |
| pH 5.0 | 25 | >60 | 15 | >60 |
| pH 6.0 | 8 | 15 | 5 | >60 |

(g)

Conclusions

Because the test was carried out on a film, rather than a tablet, the liquid was able to attack the film from both sides, rather than one side, which would be the case had a tablet been used. Accordingly, it is probable that dissolution, dispersion or disintegration took place faster in this test than would be the case in a test using a tablet. However, it is clear from these results that the pH value at which dissolution, dispersion or disintegration occurs may be controlled by the choice of alginic acid.

EXAMPLES 6–8

(a)

Preparation of Coating Solution—Example 6

9 parts of fine CMEC, 3 parts of a mixture of mono- and di-caprylates of glycerin (MGK), 0.5 part of polysorbate 80 and 1 part of carboxymethylcellulose were stirred in 86.5 parts of water, to give a solution/dispersion.

(b)

Preparation of Coating Solution—Example 7

A coating solution was prepared as in Example 6, except that sodium carboxymethylcellulose was used in place of carboxymethylcellulose.

(c)

Preparation of Coating Solution—Example 8

A coating solution was prepared as in Example 6, except that calcium carboxymethylcellulose was used in place of carboxymethylcellulose.

(d)

Preparation of Casting Film

This was carried out as in Examples 3–5(e).

(e)

Tests

These were carried out as in Examples 3–5(f) and the results are shown in Table 4.

TABLE 4

| pH of Test liquid | Ex. 6 | Ex. 7 | Ex. 8 |
| --- | --- | --- | --- |
| pH 1.2 | >60 | >60 | >60 |
| pH 4.0 | >60 | 5 | >60 |
| pH 5.0 | >60 | 5 | 20 |
| pH 6.0 | 15 | 5 | 20 |

(f)

Conclusions

It is clear from these results that the choice of salt of carboxymethylcellulose influences the pH value at which dissolution, dispersion or disintegration occurs.

EXAMPLE 9

(a)

Uncoated tablets

The uncoated tablets used were prepared as described in Example 2.

(b)

Preparation of coating solution 9 parts of fine CMEC, 3 parts of a mixture of mono- and di-caprylates of glycerin (MGK), 0.5 part of polysorbate 80 and 1 part of sodium polypectinate (Grade II, manufactured by SIGMA Chemical Company) were stirred in 86.5 parts of water, to give a solution/dispersion.

(c)

Coating

Coating was described as in Example 1. The actual weight increase of each tablet was about 29 mg.

(d)

Tests and Results

The disintegration time in minutes was determined at various pH values, using the disintegration tester prescribed by the Japanese Pharmacopoeia. The results are shown in Table 5.

TABLE 5

| pH of Test Liquid | Disc | Disintegration time (mins) |
| --- | --- | --- |
| pH 1.2 | no | >120 |
|  | yes | >120 |
| pH 4.0 | no | 34 (14–60) |
| pH 6.0 | no | 34 (14–41) |

(e)

Conclusions

The tablets of Example 9 disintegrated rapidly at pH values of 4.0 and 6.0, but not at the lower pH of 1.2, indicating that they would be suitable for Type B enteric-soluble preparations.

EXAMPLE 10

(a)

Uncoated tablets

The uncoated tablets used were prepared as described in Example 2.

(b)

Preparation of coating liquid 9 parts of fine CMEC, 3 parts of a mixture of mono- and di-caprylates of glycerin (MGK), 0.5 part of polysorbate 80, 0.5 part of alginic acid (type regular, manufactured by Kimitsu Chemical Industry Co Ltd) and 0.5 part of sodium alginate (type $IL_2$) were mixed with 86.5 parts of water to give a solution/dispersion.

(c)

Coating

The method of Example 1 was employed. The actual solid weight increase was about 26 mg per tablet.

(d)

Test and Results

The disintegration time in minutes at various pH values was determined using the disintegration tester prescribed by the Japanese Pharmacopoeia. 6 tablets were used for each test. The results are shown in Table 6.

TABLE 6

| pH of Test Liquid | Disc | Disintegration time (mins) |
| --- | --- | --- |
| pH 1.2 | no | >120 |
|  | yes | >120 |
| pH 4.0 | no | 15 (14–17) |
| pH 5.0 | no | 13 (12–14) |
| pH 6.0 | no | 12 (11–14) |

(e)

Conclusions

It is clear from the above results that the tablets undergo rapid disintegration at pH values in the range from 4.0 to 6.0, but do not disintegrate at pH 1.2; accordingly, they are useful for enteric-soluble preparations of Type B.

EXAMPLE 11

(a)
Uncoated tablets 10 parts of the same active principal as was used in Example 1 and 20 parts of a partially substituted hydroxypropylcellulose (the same as in Example 1) were mixed in a Henschel mixer for 3 minutes, and then 30 parts of water were added and the whole mixture was kneaded. The mixture was then granulated using a Tornado Mill with a screen having square apertures of dimensions $10 \times 10$ mm, and the granules were dried in a draught drier at 60° C. for 1 hour. The dried granules were passed through a Tornado Mill with circular apertures of diameter 1 mm. 30 parts of these granules, 19.75 parts of lactose and 0.25 part of magnesium stearate were mixed in a V-shaped mixer, and then the mixture was tableted to form biconvex tablets of diameter 5 mm, each weighing 50 mg. The tablets were tested to determine the disintegration time, without a disc, according to the method prescribed by the Japanese Pharmacopoeia. The disintegration time was about 4 minutes in water and in the first and second liquids of said Pharmacopoeia.

(b)
Preparation of a coating solution 9 parts of fine CMEC, 3 parts of a mixture of mono- and di-caprylates of glycerin (MGK), 0.5 part of polysorbate 80 and 1 part of sodium alginate (Type $IL_2$) were stirred in 86.5 parts of water to give a solution/dispersion.

(c)
Coating

The method of Example 1 was followed. The actual solid weight increase was about 17 mg per tablet.

(d)
Tests and Results

The disintegration time (in minutes) at various pH values was determined with a disintegration tester as prescribed by the Japanese Pharmacopoeia. The results are shown in Table 7, in which 6 tablets were used per test.

TABLE 7

| pH of Test Liquid | Disc | Disintegration time (mins) |
|---|---|---|
| pH 1.2 | no | >120 |
|  | yes | >120 |
| pH 2.0 | no | >120 |
| pH 3.0 | no | 18 (16-21) |
| pH 4.0 | no | 17 (15-19) |
| pH 5.0 | no | 17 (15-18) |
| pH 6.0 | no | 16 (16-18) |

(e)
Conclusions

The tablets obtained in Example 11 disintegrate rapidly at a pH value of 3.0 or higher, but they show a strong resistance to disintegration at pH values of 1.2 and 2.0.

The tablets were shaken for 2 hours in the first liquid of the Japanese Pharmacopoeia, with or without a disc, or in a liquid at pH 2 without a disc and then the amount of active principal remaining was determined by high pressure liquid chromatography, revealing percentage residues of 100.5, 99.2 and 100.6, respectively. It is clear from this that the tablets do not apparently disintegrate at pH values of 1.2-2.0 and, moreover, no permeation of liquid into the tablets or release of the active principal therefrom, or decomposition or dissipation of it takes place at these pH values. Thus, they are useful for Type B enteric-soluble preparations.

EXAMPLES 12-16

(a)
Preparation of coating solution—Example 12

9 parts of fine CMEC, 3 parts of a mixture of mono- and di-caprylates of glycerin (MGK), 0.5 part of polysorbate 80 and 1 part of alginic acid (Type M, manufactured by Kimitsu Chemical Industry Co., Ltd.) were stirred in 86.5 parts of water to give a solution-dispersion.

(b)
Preparation of coating solution—Example 13

1 part of alginic acid, which was the same as that used in Example 12, was dispersed in water, to which was added an aqueous solution of sodium hydroxide in an amount 25% of that required to neutralize the dispersion completely. Meanwhile, 9 parts of fine CMEC, 3 parts of a mixture of mono- and di-caprylates of glycerin (MGK) and 0.5 part of polysorbate 80 were stirred in the remaining amount of water. The two liquids were mixed to give 100 parts of a coating solution/dispersion.

(c)
Preparation of coating solution—Example 14

The method of Example 13 was repeated, except that the amount of sodium hydroxide used was 50% of that required for complete neutralisation.

(d)
Preparation of coating solution—Example 15

The method of Example 13 was repeated, except that the amount of sodium hydroxide used was 75% of that required for complete neutralisation.

(e)
Preparation of coating solution—Example 16

The method of Example 13 was repeated, except that the amount of sodium hydroxide used was sufficient for complete neutralisation.

(f)
Preparation and testing of casting films

This was performed as described in Examples 3-5.

(g)
Results

The time (minutes) required for the films to dissolve, disperse or disintegrate was measured and the results are shown in Table 8.

TABLE 8

| pH of Test liquid | Disintegration time (mins) | | | | |
|---|---|---|---|---|---|
| | Example 12 | Example 13 | Example 14 | Example 15 | Example 16 |
| pH 1.2 | >60 | >60 | >60 | >60 | >60 |
| pH 3.0 | >60 | >60 | >60 | >60 | 8 |
| pH 4.0 | 19 | 52 | 52 | >60 | 3 |
| pH 5.0 | 19 | 15 | 12 | 15 | 2 |
| pH 6.0 | 12 | 6 | 14 | 13 | 8 |

(h) Conclusions

It will be evident from the above results and the pH value at which disintegration of the film occurs changes as the degree of neutralisation of the alginic acid changes and that enteric-soluble preparations that disintegrate at any specified pH value may be obtained by controlling the degree of neutralisation.

EXAMPLE 17 AND COMPARATIVE EXAMPLE 3

(a) Preparation of a coating solution—Comparative Example 3

10 parts of hydroxypropylmethylcellulose phthalate HP 55F (Shin-Etsu Chemical Co., Ltd., Japan) and 3 parts of triacetin were dispersed in water, maintaining the liquid temperature below 15° C., to give 100 parts of a coating liquid. The liquid was maintained at a temperature below 15° C. before it was used for the preparation of films.

(b) Preparation of coating solution—Example 17

5 parts of sodium alginate (Type IL$_2$), 5 parts of hydroxypropylmethylcellulose phthalate HP 55F and 3 parts of triacetin were stirred in water to give 100 parts of a solution/dispersion.

(c) Preparation and testing of casting films

This was performed as in Examples 3–5. The film thickness was 50 micrometers. The results are shown in Table 9.

TABLE 9

| pH of Test liquid | Comp. Ex. 3 | Example 17 |
|---|---|---|
| pH 1.2 | >60 | >60 |
| pH 4.0 | >60 | >60 |
| pH 5.0 | >60 | 45 |
| pH 6.0 | 30 | 10 |

(d) Conclusions

It will be clear from the above results that the pH value at which disintegration of the film occurs may be lowered by the addition of sodium alginate.

We claim:

1. An enteric-soluble composition comprising a mixture of an enteric-soluble polymer with a polyanionic polymer which is soluble in or permeable to a liquid having a pH value less than or equal to 2.

2. A composition as claimed in claim 1, wherein said polyanionic polymer is selected from the group consisting of alginic acid, polypectinic acid, carboxymethylcellulose and salts thereof.

3. A composition as claimed in claim 1, wherein said polyanionic polymer is selected from the group consisting of alginic acid and salts thereof.

4. A composition as claimed in claim 1, wherein said enteric-soluble polymer is selected from the group consisting of ethyl acrylate/methacrylic acid copolymers, methyl acrylate/methacrylic acid copolymers, methyl methacrylate/methacrylic acid copolymers, carboxymethylethylcellulose, cellulose acetate phthalate, starch acetate phthalate, cellulose acetate succinate, styrene/maleic acid copolymers, cellulose benzoate phthalate, methylcellulose phthalate, ethylhydroxyethylcellulose phthalate, cellulose acetate maleate, hydroxypropylmethylcellulose phthalate, amylose acetate phthalate, polyvinyl alcohol phthalate, polyvinyl acetate phthalate, polyvinyl propionate phthalate, polyvinyl butyrate phthalate, polyvinylacetoacetal phthalate, polyvinylacetoacetal succinate, vinyl acetate/maleic anhydride copolymers, styrene/maleic anhydride copolymers, methyl vinyl ether/maleic anhydride copolymers, ethylene/maleic anhydride copolymers, acrylonitrile/methyl acrylate/maleic anhydride copolymers, butyl acrylate/styrene/maleic anhydride copolymers, styrene/acrylic acid polymers, butyl acrylate/styrene/acrylic acid copolymers, cellulose propionate phthalate and vinyl acetate/crotonic acid copolymers and salts thereof.

5. A composition as claimed in claim 4, wherein said polyanionic polymer is selected from the group consisting of alginic acid, polypectinic acid, carboxymethylcellulose, and salts thereof; and wherein the weight ratio of said enteric-soluble polymer to said polyanionic polymer is from 20:1 to 0.5:1.

6. A composition as claimed in claim 5, wherein said ratio is from 10:1 to 1:1.

7. A composition as claimed in claim 6, wherein said ratio is about 9:1.

8. A composition as claimed in claim 1, wherein said enteric-soluble polymer is selected from the group consisting of carboxymethylethylcellulose and salts thereof.

9. A composition as claimed in claim 1, wherein the weight ratio of said enteric-soluble polymer to said polyanionic polymer is from 20:1 to 0.5:1.

10. A composition as claimed in claim 9, wherein said ratio is from 10:1 to 1:1.

11. A composition as claimed in claim 9, wherein said ratio is about 9:1.

12. A composition as claimed in claim 1, comprising carboxymethylethylcellulose or a salt thereof and alginic acid or a salt thereof in a weight ratio of from 10:1 to 1:1.

13. A composition as claimed in claim 12, wherein said weight ratio is about 9:1.

14. An enteric-soluble composition comprising a mixture of an enteric-soluble polymer with a polyanionic polymer which is soluble in or permeable to a liquid having a pH value less than or equal to 2, said mixture being soluble in a liquid having a pH value which is above a chosen pH value within the range from 3 to 6 and being insoluble in a liquid having a pH value below said chosen pH value, wherein solubility of said polyanionic polymer and of said mixture is determined by immersing a tablet coated with said polymer or said mixture in a liquid selected from the group consisting of the first liquid of the Japanese Pharmacopoeia 10th edition, the second liquid of said Pharmacopoeia and mixtures of said first and second liquids at a temperature of 37° C. said polymer or said mixture of polymers being soluble if the average time of six such coated tablets to dissolve, disperse or disintegrate in said liquid does not exceed 60 minutes and being insoluble if said time exceeds 120 minutes and if said polymer or said mixture of polymers does not become permeable within 120 minutes.

15. A composition as claimed in claim 14, wherein said polyanionic polymer is selected from the group consisting of alginic acid, polypectinic acid, carboxymethylcellulose and salts thereof.

16. A composition as claimed in claim 14, wherein said polyanionic polymer is selected from the group consisting of alginic acid and salts thereof.

17. A composition as claimed in claim 14, wherein said enteric-soluble polymer is selected from the group consisting of ethyl acrylate/methacrylic acid copolymers, methyl acrylate/methacrylic acid copolymers, methyl methacrylate/methacrylic acid copolymers, carboxymethylethylcellulose, cellulose acetate phthalate, starch acetate phthalate, cellulose acetate succinate, styrene/maleic acid copolymers, cellulose benzoate phthalate, methylcellulose phthalate, ethylhydroxyethylcellulose phthalate, cellulose acetate maleate, hydroxypropylmethylcellulose phthalate, amylose acetate phthalate, polyvinyl alcohol phthalate, polyvinyl acetate phthalate, polyvinyl propionate phthalate, polyvinyl butyrate phthalate, polyvinylacetoacetal phthalate, polyvinylacetoacetal succinate, vinyl acetate/maleic anhydride copolymers, styrene/maleic anhydride copolymers, methyl vinyl ether/maleic anhydride copolymers, ethylene/maleic anhydride copolymers, acrylonitrile/methyl acrylate/maleic anhydride copolymers, butyl acrylate/styrene/maleic anhydride copolymers, styrene/acrylic acid copolymers, butyl acrylate/styrene/acrylic acid copolymers, cellulose propionate phthalate and vinyl acetate/crotonic acid copolymers and salts thereof.

18. A composition as claimed in claim 17, wherein said polyanionic polymer is selected from the group consisting of alginic acid, polypectinic acid, carboxymethylcellulose, and salts thereof; and wherein the weight ratio of said enteric-soluble polymer to said polyanionic polymer is from 20:1 to 0.5:1.

19. A composition as claimed in claim 18, wherein said ratio is from 10:1 to 1:1.

20. A composition as claimed in claim 19, wherein said ratio is about 9:1.

21. A composition as claimed in claim 14, wherein said enteric-soluble polymer is selected from the group consisting of carboxymethylethylcellulose and salts thereof.

22. A composition as claimed in claim 14, wherein the weight ratio of said enteric-soluble polymer to said polyanionic polymer is from 20:1 to 0.5:1.

23. A composition as claimed in claim 22, wherein said ratio is from 10:1 to 1:1.

24. A composition as claimed in claim 22, wherein said ratio is about 9:1.

25. A composition as claimed in claim 14, comprising carboxymethylethylcellulose or a salt thereof and alginic acid or a salt thereof in a weight ratio of from 10:1 to 1:1.

26. A composition as claimed in claim 25, wherein said weight ratio is about 9:1.

27. An enteric-soluble preparation in unit dosage form comprising an active ingredient surrounded by a membrane formed from an enteric-soluble composition comprising a mixture of an enteric-soluble polymer with a polyanionic polymer which is soluble in or permeable to a liquid having a pH value less than or equal to 2.

28. A preparation as claimed in claim 27, wherein said polyanionic polymer is selected from the group consisting of alginic acid, polypectinic acid, carboxymethylcellulose and salts thereof.

29. A preparation as claimed in claim 27, wherein said polyanionic polymer is selected from the group consisting of alginic acid and salts thereof.

30. A preparation as claimed in claim 27, wherein said enteric-soluble polymer is selected from the group consisting of ethyl acrylate/methacrylic acid copolymers, methyl acrylate/methacrylic acid copolymers, methyl methacrylate/methacrylic acid copolymers, carboxymethylethylcellulose, cellulose acetate phthalate, starch acetate phthalate, cellulose acetate succinate, styrene/maleic acid copolymers, cellulose benzoate phthalate, methylcellulose phthalate, ethylhydroxyethylcellulose phthalate, cellulose acetate maleate, hydroxypropylmethylcellulose phthalate, amylose acetate phthalate, polyvinyl alcohol phthalate, polyvinyl acetate phthalate, polyvinyl propionate phthalate, polyvinyl butyrate phthalate, polyvinylacetoacetal phthalate, polyvinylacetoacetal succinate, vinyl acetate/maleic anhydride copolymers, styrene/maleic anhydride copolymers, methyl vinyl ether/maleic anhydride copolymers, ethylene/maleic anhydride copolymers, acrylonitrile/methyl acrylate/maleic anhydride copolymers, butyl acrylate/styrene/maleic anhydride copolymers, styrene/acrylic acid copolymers, butyl acrylate/styrene/acrylic acid copolymers, cellulose propionate phthalate and vinyl acetate/crotonic acid copolymers and salts thereof.

31. A preparation as claimed in claim 30, wherein said polyanionic polymer is selected from the group consisting of alginic acid, polypectinic acid, carboxymethylcellulose, and salts thereof; and wherein the weight ratio of said enteric-soluble polymer to said polyanionic polymer is from 20:1 to 0.5:1.

32. A preparation as claimed in claim 31, wherein said ratio is from 10:1 to 1:1.

33. A preparation as claimed in claim 32, wherein said ratio is about 9:1.

34. A preparation as claimed in claim 27, wherein said enteric-soluble polymer is selected from the group consisting of carboxymethylethylcellulose and salts thereof.

35. A preparation as claimed in claim 27, wherein the weight ratio of said enteric-soluble polymer to said polyanionic polymer is from 20:1 to 0.5:1.

36. A preparation as claimed in claim 35, wherein said ratio is from 10:1 to 1:1.

37. A preparation as claimed in claim 35, wherein said ratio is about 9:1.

38. A preparation as claimed in claim 27, wherein said composition comprises carboxymethylethylcellulose or a salt thereof and alginic acid or a salt thereof in a weight ratio of from 10:1 to 1:1.

39. A preparation as claimed in claim 38, wherein said weight ratio is about 9:1.

40. A preparation as claimed in claim 27, wherein said mixture is soluble in a liquid having a pH value which is above a chosen pH value within the range from 3 to 6 and is insoluble in a liquid having a pH value below said chosen pH value, wherein solubility of said polyanionic polymer and of said mixture is determined by immersing a tablet coated with said polymer or said mixture in a liquid selected from the group consisting of the first liquid of the Japanese Pharmacopoeia 10th edition, the second liquid of said Pharmacopoeia and mixtures of said first and second liquids at a temperature of 37° C., said polymer or said mixture of polymers being soluble if the average time of six such coated tablets to dissolve, disperse or disintegrate in said liquid does not exceed 60 minutes and being insoluble if said time exceeds 120 minutes and if said polymer or said mixture of polymers does not become permeable within 120 minutes.

* * * * *